United States Patent
Jeong et al.

(10) Patent No.: US 10,765,194 B2
(45) Date of Patent: *Sep. 8, 2020

(54) METHOD OF PREPARING DRY HYDROGEL SHEET AND DRY HYDROGEL SHEET PREPARED BY THE SAME

(71) Applicant: LOTTE FINE CHEMICAL CO., LTD., Ulsan (KR)

(72) Inventors: Ji Seon Jeong, Incheon (KR); Ju Hee Shin, Incheon (KR); Sung Hwan Bang, Incheon (KR); Ju Young Jung, Incheon (KR); Kil Seuk Byun, Yongin-Si (KR); Kyong Min Lee, Anyang-si (KR)

(73) Assignee: LOTTE FINE CHEMICAL CO., LTD., Ulsan (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/773,761

(22) PCT Filed: Oct. 27, 2016

(86) PCT No.: PCT/KR2016/012149
§ 371 (c)(1),
(2) Date: May 4, 2018

(87) PCT Pub. No.: WO2017/078327
PCT Pub. Date: May 11, 2017

(65) Prior Publication Data
US 2018/0325244 A1 Nov. 15, 2018

(30) Foreign Application Priority Data
Nov. 6, 2015 (KR) .......................... 10-2015-0156130

(51) Int. Cl.
*A45D 44/00* (2006.01)
*A45D 44/22* (2006.01)
(Continued)

(52) U.S. Cl.
CPC ........... *A45D 44/002* (2013.01); *A45D 37/00* (2013.01); *A45D 44/22* (2013.01); *A61K 8/0212* (2013.01);
(Continued)

(58) Field of Classification Search
CPC .................. A45D 44/22; A45D 37/00; A45D 2200/1027; A45D 2200/1036;
(Continued)

(56) References Cited

U.S. PATENT DOCUMENTS

2007/0154527 A1* 7/2007 Myers .................. A61K 8/0208
424/443
2010/0189993 A1* 7/2010 Mori ........................ C08J 7/047
428/317.5
(Continued)

FOREIGN PATENT DOCUMENTS

EP 0714656 B1 * 2/2001 ........... A61K 9/4816
JP 2005-022980 A 1/2005
(Continued)

OTHER PUBLICATIONS

International Search Report issued in PCT/KR2016/012149 dated Feb. 10, 2017 (2 pages).
(Continued)

*Primary Examiner* — Jianfeng Song
(74) *Attorney, Agent, or Firm* — Osha Liang LLP

(57) ABSTRACT

The present invention relates to a method of preparing a dry hydrogel sheet including the steps of: preparing a cellulose ether dispersion solution; transferring the dispersion solution to a coater while maintaining the temperature of the dispersion solution in the range of a gelation temperature of the dispersion solution to a boiling point of a dispersion medium; applying the dispersion solution transferred to the coater as a sheet; preparing a hydrogel sheet by cooling the
(Continued)

applied dispersion solution to induce gelation; and drying the hydrogel sheet. Since the dry hydrogel sheet prepared by the method has a low moisture content, it is possible to ensure the stability of active ingredients, quantify functional components to be applied to the dry hydrogel sheet, and ensure the uniformity of the surface appearance and thickness of the dry hydrogel sheet, which results in the improvement of the quality of a final product.

5 Claims, 4 Drawing Sheets

(51) Int. Cl.
  *A61K 8/02*  (2006.01)
  *A61K 9/70*  (2006.01)
  *C08J 3/075*  (2006.01)
  *C08J 5/18*  (2006.01)
  *A45D 37/00*  (2006.01)
  *A61Q 19/00*  (2006.01)
  *A61K 9/00*  (2006.01)
  *A61L 15/60*  (2006.01)
  *A61L 15/28*  (2006.01)
  *A61K 8/73*  (2006.01)
  *A61L 26/00*  (2006.01)

(52) U.S. Cl.
  CPC ............ *A61K 8/731* (2013.01); *A61K 9/0014* (2013.01); *A61K 9/7007* (2013.01); *A61K 9/7046* (2013.01); *A61L 15/28* (2013.01); *A61L 15/60* (2013.01); *A61L 26/008* (2013.01); *A61L 26/0023* (2013.01); *A61Q 19/00* (2013.01); *C08J 3/075* (2013.01); *C08J 5/18* (2013.01); *A45D 2200/1027* (2013.01); *A45D 2200/1036* (2013.01); *C08J 2301/28* (2013.01)

(58) Field of Classification Search
  CPC .... A61K 9/7007; A61K 8/731; A61K 8/0212; C08J 5/18; C08J 2301/28; A61Q 19/00
  See application file for complete search history.

(56) References Cited

U.S. PATENT DOCUMENTS

2013/0295188 A1* 11/2013 Cade ...................... A61K 47/10
                      424/494
2014/0239536 A1* 8/2014 Yoo ......................... C08L 39/06
                      264/129

FOREIGN PATENT DOCUMENTS

| | | |
|---|---|---|
| JP | 2006-123173 A | 5/2006 |
| KR | 10-2001-0029792 A | 4/2001 |
| KR | 10-2009-0016459 A | 2/2009 |
| KR | 10-2013-0036543 A | 4/2013 |
| KR | 10-2014-0108803 A | 9/2014 |
| KR | 10-1563325 B1 | 10/2015 |
| KR | 10-2016-0056005 A | 5/2016 |

OTHER PUBLICATIONS

Written Opinion of the International Searching Authority issued in PCT/KR2016/012149 dated Feb. 10, 2017 (4 pages).

* cited by examiner

[FIG. 1]

[FIG. 2]

【FIG. 3】
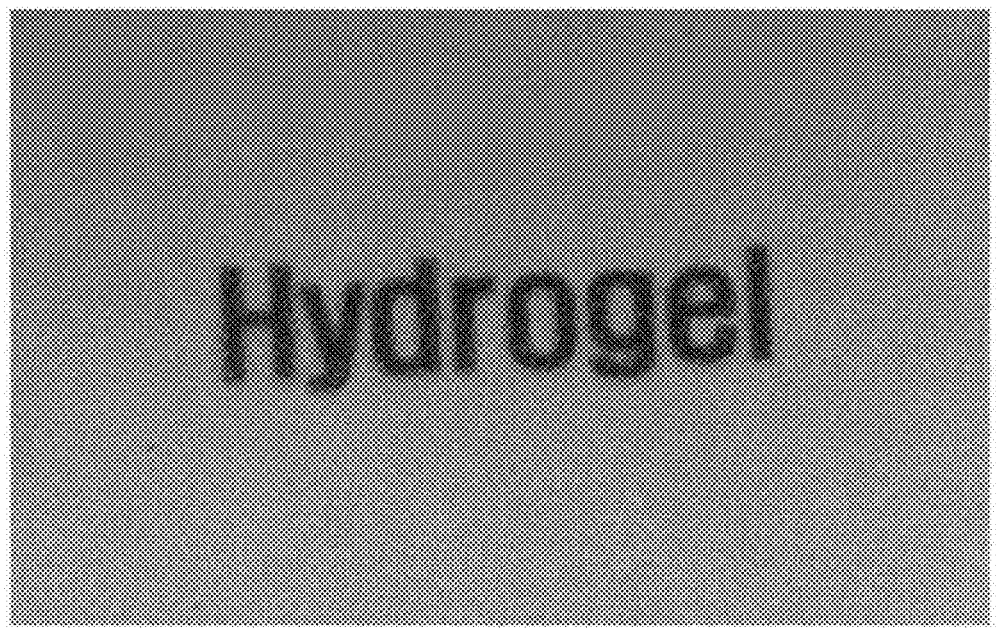
【FIG. 4】
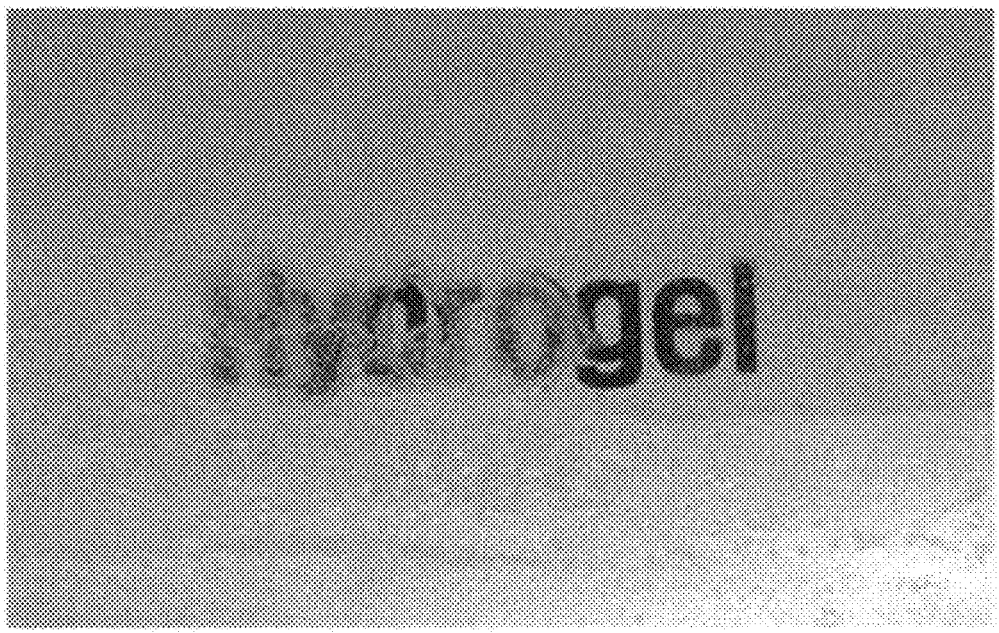

[FIG. 5]
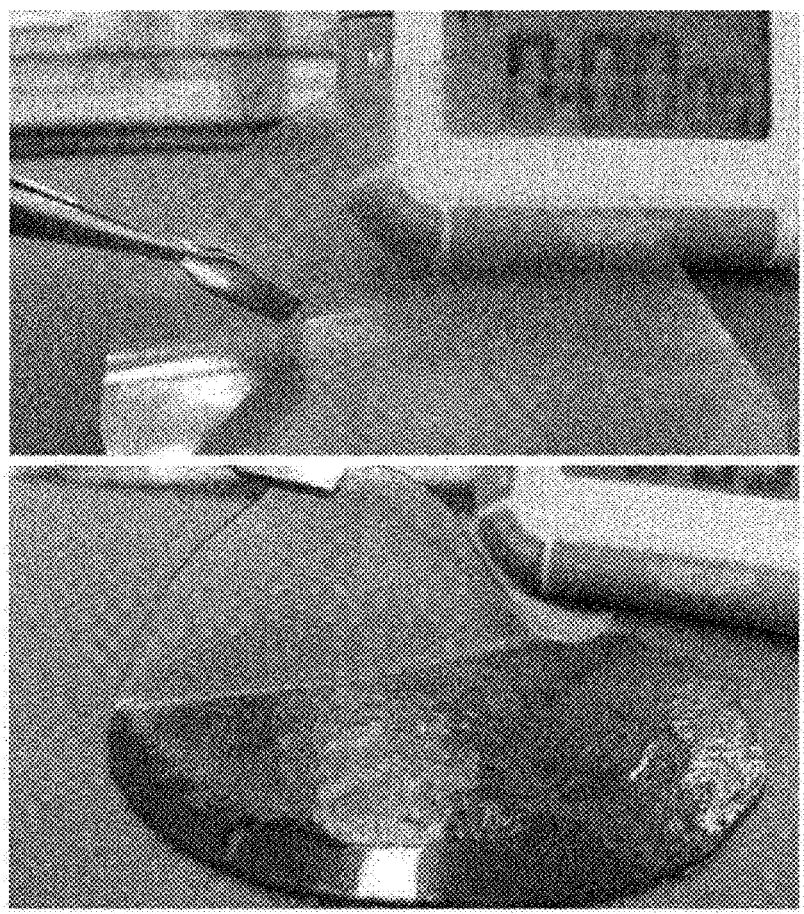

METHOD OF PREPARING DRY HYDROGEL SHEET AND DRY HYDROGEL SHEET PREPARED BY THE SAME

TECHNICAL FIELD

The present invention relates to a method of preparing a dry hydrogel sheet and a dry hydrogel sheet prepared by the same.

BACKGROUND ART

A hydrogel is a network of hydrophilic polymer chains in which water is the dispersion medium. The hydrogel is not dissolved but swelled in water so that it can contain a large amount of water in the structure thereof and thus it possesses a degree of flexibility very similar to that of natural tissue.

The hydrogel has been used in the medical and pharmaceutical field, such as the fields of tissue engineering, cell culture, sustained-release drug delivery systems, biosensors, soft lenses, medical electrodes, and the like, due to its unique hydrophilicity and flexibility, and has also been applied in various fields including absorbents for hygienic goods, delivery media of cosmetic agents, and the like.

As the conventional technologies using the hydrogel, Patent Document 1 (Korean Laid-Open Patent Publication No. 10-2014-0108803) discloses a method of preparing a hydrogel film, which includes preparing a resin for a hydrogel; forming a hydrogel by applying the resin for a hydrogel onto a surface of a release film and then drying the same; and crosslinking and swelling the hydrogel by infiltrating the hydrogel formed on the surface of a release film with a crosslinking-swelling agent. In this case, the resin for a hydrogel includes 1 to 40 wt % of a polymer resin containing one or more selected from a water-soluble polymer and a natural polymer, 0.05 to 20 wt % of sodium alginate, 0.1 to 20 wt % of a plasticizer, 0.1 to 20 wt % of a moisturizer, and 20 to 98 wt % of distilled water. Regarding Patent Document 1, it is described that a hydrogel film having excellent mechanical strength, good flexibility, excellent adhesion to skin, excellent comfort, and the like may be provided.

In addition, Patent Document 2 (Korean Registered Patent No. 10-1563325) discloses a method of preparing an antipyretic patch, which includes applying an adhesive onto one surface of an urethane film and then adhering a nonwoven fabric thereto; mixing a hydrogel with a functional material having antipyretic efficacy to prepare a functional hydrogel; applying the functional hydrogel onto a surface of the nonwoven fabric or one surface of a release film and then bringing the functional hydrogel in close contact with the nonwoven fabric or the release film in such a way that the functional hydrogel is positioned between the nonwoven fabric and the release film to prepare a patch sheet; thermally treating and drying the patch sheet to form a semisolid-phase functional hydrogel from the functional hydrogel; and cutting the patch sheet including the semisolid-phase functional hydrogel into a shape conforming with an application site of the human body. In this case, the hydrogel includes 5 to 15 wt % of polyacrylic acid, 10 to 40 wt % of glycerin, 1 to 10 wt % of sodium hydroxide, 0.1 to 3 wt % of agar, 0.1 to 3 wt % of Polysorbate 60, and water as the remainder, and the functional material is prepared by mixing a functional mixture comprising any one of menthoxypropanediol, menthyl lactate and mixture thereof; and oriental plant extracts comprising two or more selected from a cucumber extract, an aloe extract, a *Tricholoma matsutake* extract, a *Phellodendron amurense* bark extract, a carrot root extract, and a *Lycium chinense* fruit extract. The hydrogel and the functional material are mixed in a ratio of 97 to 99 wt % and 1 to 3 wt %, respectively. Patent Document 2 describes that when the antipyretic patch prepared by the above method is applied to a corresponding site in the human body, fever may be effectively reduced.

However, when a functional component is applied to a hydrogel as prior-art documents, the concentration of an active ingredient may be diluted or the stability of an active ingredient may be adversely affected within the shelf life of a product. For example, since the hydrogel has a high moisture content, decomposition caused by proliferation of microorganisms may occur, and high distribution costs are also required.

PRIOR-ART DOCUMENTS

Patent Documents (Patent Document 1) KR1020140108803 A
(Patent Document 2) KR101563325 B

DISCLOSURE

Technical Problem

It is an object of the present invention to provide a method of preparing a dry hydrogel sheet which is capable of solving a problem of a conventional hydrogel such as decomposition caused by proliferation of microorganisms occurring due to a high moisture content by lowering a moisture content, and to which a quantified amount of functional component can be applied.

It is another object of the present invention to provide a method of preparing a dry hydrogel sheet which has a uniform surface appearance and ensures the uniformity of a thickness by adjusting the temperature of a dispersion solution.

It is still another object of the present invention to provide a dry hydrogel sheet prepared by the above-described method.

Technical Solution

The present invention is designed to achieve the above objects and provides a method of preparing a dry hydrogel sheet, which includes preparing a cellulose ether dispersion solution; transferring the dispersion solution to a coater while maintaining a temperature of the dispersion solution in a range of a gelation temperature of the dispersion solution to a boiling point of a dispersion medium; applying the dispersion solution transferred to the coater as a sheet; preparing a hydrogel sheet by cooling the applied dispersion solution to induce gelation; and drying the hydrogel sheet.

The method may further include deaerating the dispersion solution to remove air bubbles from the dispersion solution.

The cellulose ether dispersion solution may include a cellulose ether, a gelling agent, a gelling promoter, and a dispersion medium. The cellulose ether may be any one or two or more selected from the group consisting of hydroxypropyl methyl cellulose, hydroxyethyl cellulose, hydroxypropyl cellulose, and carboxymethyl cellulose.

The coater may be selected from the group consisting of a gravure coater, a comma coater, a slot-die coater, and a spray coater.

It is preferable that the temperature ranging from a gelation temperature of the dispersion solution to a boiling point of the dispersion medium is 50 to 100° C.

The cooling of the dispersion solution may be carried out by any one method selected from natural cooling, cooling with a cooling tunnel, and a combination thereof. The drying of the hydrogel sheet may be carried out by any one method selected from the group consisting of hot air drying, infrared drying, and microwave drying, or a combination of two or more thereof.

In addition, the present invention provides a dry hydrogel sheet prepared by the above-described method. In this case, it is preferable that the sheet has a thickness of 10 to 200 μm.

Additionally, the present invention provides a cosmetic mask pack or a medical patch including the dry hydrogel sheet.

Advantageous Effects

A dry hydrogel sheet prepared by the method according to the present invention has a low moisture content and thus can solve a problem of a conventional hydrogel such as decomposition caused by proliferation of microorganisms occurring due to a high moisture content. Also, the volume and weight of the hydrogel sheet significantly decrease so that distribution costs can be reduced.

In addition, a quantified amount of functional component can be applied to the dry hydrogel sheet so that a problem of a conventional hydrogel sheet, such as a concentration dilution of an active ingredient occurring when a functional component is applied to the hydrogel sheet, can be solved.

Additionally, the uniformity of the surface and thickness of the dry hydrogel sheet can be ensured by appropriately adjusting the temperature of a cellulose ether dispersion solution so that the quality of a final product can be improved.

DESCRIPTION OF DRAWINGS

FIG. 1 is an image of a dry hydrogel sheet prepared according to the Example.

FIG. 2 is an image of a dry hydrogel sheet prepared according to the Comparative Example.

FIG. 3 is an image obtained by photographing the dry hydrogel sheet of FIG. 1, which is placed on the word "Hydrogel".

FIG. 4 is an image obtained by photographing the dry hydrogel sheet of FIG. 2, which is placed on the word "Hydrogel".

FIG. 5 is a set of images showing a dry hydrogel sheet (left) and the same hydrogel sheet gelated due to applied moisture (right).

MODES OF THE INVENTION

The present invention relates to a method of preparing a dry hydrogel sheet and a dry hydrogel sheet prepared by the same.

First, the method of preparing a dry hydrogel sheet will be described. The method includes preparing a cellulose ether dispersion solution; transferring the dispersion solution to a coater while maintaining a temperature of the dispersion solution in a range of a gelation temperature of the dispersion solution to a boiling point of a dispersion medium; applying the transferred dispersion solution as a sheet; preparing a hydrogel sheet by cooling the applied dispersion solution to induce gelation; and drying the hydrogel sheet.

Hereinafter, the method of preparing a dry hydrogel sheet according to one embodiment of the present invention will be described in detail.

(1) Preparation of Dispersion Solution

In this step, a cellulose ether dispersion solution is prepared. The cellulose ether dispersion solution may include a cellulose ether, a gelling agent, a gelling promoter, and a dispersion medium. The preparation of the cellulose ether dispersion solution may include preparing a preliminary mixture by mixing a cellulose ether, a gelling agent, and a gelling promoter; and dispersing the preliminary mixture in a dispersion medium.

The method of preparing a dry hydrogel sheet according to the present invention may further include deaerating the dispersion solution to remove air bubbles from the dispersion solution. The deaeration is carried out preferably at 55 to 65° C. for 20 to 60 minutes. When a preliminary mixture is prepared and then dispersed in a dispersion medium as described above, a process time required to carry out the deaeration may be shortened compared to when a cellulose ether, a gelling agent, and a gelling promoter are dispersed in a dispersion medium one at a time.

The cellulose ether refers to a cellulose derivative produced by etherifying the hydroxyl groups of cellulose. The properties of cellulose ether are water-soluble and swelled after absorbing water. As the cellulose ether, any one or two or more selected from the group consisting of hydroxypropyl methyl cellulose, hydroxyethyl cellulose, hydroxypropyl cellulose, and carboxymethyl cellulose may be used, and preferably, hydroxypropyl methyl cellulose is used.

The gelling agent is used to form a gel, adjust strength, control syneresis, and improve comfort, and a natural polymer may be used rather than a water-soluble synthetic polymer in consideration of skin toxicity. As the natural polymer, any one or two or more selected from the group consisting of carrageenan, locust bean gum, mannose, and water-chestnut flour may be used.

The gelling promoter serves to crosslink the natural polymer. The gelling promoter may be a Group 1 or 2 metal salt, and for example, any one or two or more selected from the group consisting of magnesium chloride, potassium chloride, calcium chloride, and sodium chloride may be used.

The dispersion medium may be water, more preferably, 85° C. or more hot water.

(2) Transference of Dispersion Solution

In this step, the dispersion solution is transferred to a coater while maintaining the temperature of the dispersion solution in a range of a gelation temperature of the dispersion solution to a boiling point of the dispersion medium.

In the preparation of the dry hydrogel sheet according to the present invention, it is very important to adjust the temperature of the cellulose ether dispersion solution. When the temperature of the dispersion solution is less than the gelation temperature thereof, gelation proceeds during a transference process to cause a non-uniform concentration of solids, resulting in adverse effects on surface characteristics of a final film. On the other hand, when the temperature of the dispersion solution is greater than the boiling point of the dispersion medium, the dispersion medium is evaporated to cause a change in a concentration, and thus a uniform product may not be obtained. In consideration of the above problems, a temperature ranging from a gelation temperature of the dispersion solution to a boiling point of the dispersion medium is preferably 50 to 100° C., more preferably, 55 to 90° C.

Specifically, FIG. 1 illustrates an image of a dry hydrogel sheet when the temperature of a cellulose ether dispersion solution is maintained within the above range. It can be seen through FIG. 1 that a dry hydrogel sheet prepared under this condition has a uniform surface appearance. On the other hand, FIG. 2 illustrates an image of a dry hydrogel sheet when the temperature of a dispersion solution is out of the above range. It can be seen through FIG. 2 that a dry hydrogel sheet prepared under this condition has a non-uniform and rough surface appearance.

As the coater, a coater commonly used in the related art may be used without limitation. For example, the coater may be selected from the group consisting of a gravure coater, a comma coater, a slot-die coater, and a spray coater.

(3) Application of Dispersion Solution

In this step, the dispersion solution transferred to the coater is applied as a sheet. The dispersion solution may be applied onto a release paper, and the dispersion solution thus applied preferably has a thickness of 0.1 to 10 mm. The thickness of the dispersion solution affects a thickness of a dry hydrogel sheet, which is a final product, after being impregnated with water, i.e., a thickness of a hydrogel sheet to be applied to the skin. That is, when the thickness of the dispersion solution is less than 0.1 mm, a hydrogel sheet to be applied to the skin may be torn due to reduced strength. On the other hand, when the thickness the dispersion solution is greater than 10 mm, adhesion of a hydrogel sheet to skin may be significantly reduced, and efficiency of releasing active ingredients may also be degraded.

(4) Preparation of Hydrogel Sheet

In this step, the dispersion solution applied according to the step (3) is cooled and gelated to prepare a hydrogel sheet.

In this case, the cooling of the dispersion solution may be carried out by any one method selected from natural cooling, cooling with a cooling tunnel, and a combination thereof.

(5) Drying of Hydrogel Sheet

In this step, the hydrogel sheet prepared according to the step (4) is dried to prepare a dry hydrogel sheet as a final product.

In this case, the drying of the hydrogel sheet may be carried out by any one method selected from the group consisting of hot air drying, infrared drying, and microwave drying, or a combination of two or more thereof. For example, when a hot air drying method is used, the drying process may be carried out at 120 to 180° C. for 1 to 60 minutes.

In addition, the present invention provides a dry hydrogel sheet prepared according to the above-described method.

The dry hydrogel sheet exhibits a reversible property in which it is gelated when impregnated with water. Therefore, for practically applying the dry hydrogel sheet to the skin, a subject uses the dry hydrogel sheet after impregnation with a liquid containing functional components. Through this process, the dry hydrogel sheet is gelated and thus may be used as a common hydrogel sheet in a gel state. Specifically, FIG. 5 is a set of images showing a dry hydrogel sheet (left) and the same hydrogel sheet gelated due to applied moisture (right).

The dry hydrogel sheet preferably has a thickness of 10 to 200 μm. When the thickness of the dry hydrogel sheet is less than 10 μm, the thickness of the hydrogel sheet in a gel state becomes thinner so that it may be torn due to reduced strength. On the other hand, when the thickness of the dry hydrogel sheet is greater than 200 μm, adhesion of a hydrogel sheet in a gel state to skin may be significantly reduced, and efficiency of releasing active ingredients may also be degraded.

In the case of a conventional hydrogel sheet, there is a problem of dilution of the concentration of an active ingredient occurring when a functional component is applied to the hydrogel sheet. On the other hand, in the case of the dry hydrogel sheet according to the present invention, a quantified amount of functional component may be applied. The dry hydrogel sheet has a low moisture content and thus a problem of decomposition caused by proliferation of microorganisms occurring due to a high moisture content can be solved. Also, the volume and weight of the hydrogel sheet significantly decrease so that distribution costs can be reduced.

In addition, the present invention provides a cosmetic mask pack or a medical patch including the dry hydrogel sheet. However, the use of the dry hydrogel sheet is not limited to the above applications, and the dry hydrogel sheet may be widely applied to various products in the fields such as tissue engineering, cell culture, biosensors, soft lenses, medical electrodes, absorbents for hygienic goods, and the like.

Hereinafter, the present invention will be described in more detail with reference to examples of the present invention. However, the present invention is not limited by the following examples.

EXAMPLE

Hydroxypropyl methyl cellulose (HPMC; HPMC 2910 commercially available from Lotte Fine Chemical Co., Ltd.), carrageenan, and potassium chloride (KCl) were mixed at a ratio of 0.3 mole of carrageenan and 0.07 mole of KCl per 1 mole of a glucose unit of HPMC to prepare a preliminary mixture (HPMC:carrageenan:KCl=1:0.3:0.07). Subsequently, the preliminary mixture was dispersed at a solid concentration of 5 wt % in 85° C. hot water (a gelation temperature of the preliminary mixture is 45° C.), and then maintained at 60° C. until all air bubbles in the dispersion solution were removed.

The dispersion solution from which air bubbles were removed was transferred to a coater (comma-coater) set to 70° C.

The dispersion solution transferred to the coater was transferred to a coating solution supply unit and applied as a sheet on a release paper. In this case, the dispersion solution was applied with a thickness of 0.2 mm.

The dispersion solution applied on the release paper was naturally cooled and gelated to prepare a hydrogel sheet during a transference process.

The hydrogel sheet was dried using a hot air dryer at 170° C. for 4 minutes to prepare a dry hydrogel sheet.

Comparative Example

A dry hydrogel sheet was prepared in the same manner as in the example except that the dispersion solution from which air bubbles were removed was transferred to a coater set to 40° C.

<Evaluation Method>

Thickness of Dry Hydrogel Sheet

The thicknesses of dry hydrogel sheets with a size of 300×300 mm according to the example and the comparative example were measured using a thickness gauge (No. 547-401 commercially available from Mitutoyo). In this case, the thicknesses at 15 points randomly selected in the dry hydrogel sheet were measured. The thickness measured at each point and the average and standard deviation thereof are shown in the following Table 1.

TABLE 1

| Point No. | Comparative Example (μm) | Example (μm) |
| --- | --- | --- |
| 1 | 36 | 32 |
| 2 | 23 | 31 |
| 3 | 42 | 33 |
| 4 | 45 | 31 |
| 5 | 37 | 32 |
| 6 | 46 | 34 |
| 7 | 37 | 32 |
| 8 | 36 | 31 |
| 9 | 38 | 31 |
| 10 | 36 | 32 |
| 11 | 37 | 31 |
| 12 | 35 | 34 |
| 13 | 27 | 32 |
| 14 | 5 | 36 |
| 15 | 9 | 34 |
| Average | 32.6 | 32.4 |
| Standard deviation | 11.9 | 1.5 |

As shown in Table 1, it can be seen that the dry hydrogel sheet according to the present invention had an average thickness similar to that of a dry hydrogel sheet according to the comparative example, but exhibited a significantly lower standard deviation compared to a dry hydrogel sheet according to the comparative example. Accordingly, it can be confirmed that a dry hydrogel sheet with a uniform thickness distribution can be prepared according to the method of the present invention.

In addition, when FIGS. 1 and 2 illustrating images of dry hydrogel sheets according to the example and the comparative example are compared, it can also be confirmed from their appearances that the dry hydrogel sheet according to the example had a more uniform surface than a dry hydrogel sheet according to the comparative example. Also, FIGS. 3 and 4 are images obtained by photographing the dry hydrogel sheets of FIGS. 1 and 2 placed on the word "Hydrogel". It can be confirmed through FIGS. 3 and 4 that in the case of the dry hydrogel sheet according to the example, the word was uniformly seen through the sheet, whereas in the case of a dry hydrogel sheet according to the comparative example, the word was not uniformly seen through the sheet. This proves that the hydrogel in a dry hydrogel sheet according to the comparative example is not uniformly distributed.

The examples disclosed in the present invention are intended to illustrate, not limit, the technical spirit of the present invention, and the scope of the present invention should be interpreted by the appended claims and to encompass all equivalents falling within the scope of present invention.

The invention claimed is:

1. A method of preparing a dry hydrogel sheet comprising:
preparing a cellulose ether dispersion solution;
transferring the dispersion solution to a coater while maintaining a temperature of the dispersion solution in a range from a gelation temperature of the dispersion solution to a boiling point of water;
applying the dispersion solution transferred to the coater as a sheet;
preparing a hydrogel sheet by cooling the applied dispersion solution to induce gelation; and
drying the hydrogel sheet,
wherein the cellulose ether dispersion solution consisting of a cellulose ether, a gelling agent, a gelling promoter and water,
wherein the cellulose ether is any one or two or more selected from the group consisting of hydroxypropyl methyl cellulose, hydroxyethyl cellulose, hydroxypropyl cellulose, and carboxymethyl cellulose, and
wherein the range from the gelation temperature of the dispersion solution to the boiling point of water is between 55 and 90° C.

2. The method according to claim 1, further comprising deaerating the dispersion solution to remove air bubbles from the dispersion solution.

3. The method according to claim 1, wherein the coater is selected from the group consisting of a gravure coater, a comma coater, a slot-die coater, and a spray coater.

4. The method according to claim 1, wherein the cooling of the dispersion solution is carried out by any one method selected from natural cooling, cooling with a cooling tunnel, and a combination thereof.

5. The method according to claim 1, wherein the drying of the hydrogel sheet is carried out by any one method selected from the group consisting of hot air drying, infrared drying, and microwave drying, or a combination of two or more thereof.

* * * * *